United States Patent

Gerson

Patent Number: 5,119,809
Date of Patent: Jun. 9, 1992

[54] MOUTH-TO-MOUTH WITH VALVE AND BARRIER

[76] Inventor: Howard J. Gerson, 9957 Westgate, Lenexa, Kans. 66215

[21] Appl. No.: 706,385
[22] Filed: May 28, 1991
[51] Int. Cl.$^5$ .................. A61M 16/00; A62B 9/06
[52] U.S. Cl. .................. 128/203.11; 128/202.28; 128/207.14
[58] Field of Search .................. 128/202.28, 203.11, 128/202.29, 207.14, 207.16

[56] References Cited

U.S. PATENT DOCUMENTS

| | | | |
|---|---|---|---|
| 2,995,131 | 12/1961 | Elam et al. | 128/202.28 |
| 3,021,836 | 2/1962 | Marsden | 128/202.28 |
| 3,057,347 | 10/1962 | McGee | 128/207.14 |
| 3,137,293 | 6/1964 | Green | 128/202.28 |
| 3,303,845 | 2/1967 | Detmer | 128/202.28 |
| 3,387,624 | 6/1968 | Soucy | 137/525.1 |
| 3,407,810 | 10/1968 | Waldrep | 128/202.28 |
| 3,473,532 | 10/1969 | Eisenberg | 128/DIG. 24 |
| 3,518,989 | 7/1970 | Sealer | 128/202.28 |
| 3,626,936 | 12/1971 | Barker | 128/202.28 |
| 3,724,461 | 4/1973 | Eisenberg | 128/DIG. 24 |
| 3,802,428 | 4/1974 | Sherman | 128/202.28 |
| 3,957,046 | 5/1976 | Harris | 128/202.28 |
| 4,360,017 | 11/1982 | Barlett | 128/202.28 |
| 4,535,765 | 8/1985 | Paoluccio et al. | 128/203.11 |
| 4,579,114 | 4/1986 | Gray et al. | 128/203.11 |
| 4,607,663 | 8/1986 | Raftis et al. | 137/846 |
| 4,622,964 | 11/1986 | Flynn | 128/205.24 |
| 4,697,587 | 10/1987 | Marinkovich | 128/203.11 |
| 4,819,627 | 4/1989 | Connors | 128/203.11 |
| 4,819,628 | 4/1989 | Eisenberg et al. | 128/203.11 |
| 4,858,605 | 8/1989 | Levy | 128/203.11 |
| 4,909,245 | 3/1990 | Wollenhaupt | 128/203.11 |
| 4,969,456 | 11/1990 | Cooper | 128/203.11 |

FOREIGN PATENT DOCUMENTS

| | | | |
|---|---|---|---|
| 240878 | 10/1962 | Australia | 128/202.28 |
| 303367 | 2/1989 | European Pat. Off. | 128/202.28 |
| 1204930 | 1/1960 | France | 128/202.28 |
| 1183054 | 3/1970 | United Kingdom | 128/202.28 |
| 2204498 | 11/1988 | United Kingdom | 128/202.28 |

*Primary Examiner*—Edgar S. Burr
*Assistant Examiner*—Kimberly L. Asher
*Attorney, Agent, or Firm*—Litman, McMahon & Brown

[57] ABSTRACT

A mouth-to-mouth barrier for facilitating mouth-to-mouth resuscitation of a heart attack or accident victim or the like while protecting a rescuer, includes a transparent shield and a breathing tube extending through an opening in the shield. A light weight air impermeable plate is positioned within the breathing tube and is free to move between a lower position which permits air to flow from the rescuer around the plate and through the tube and an upper position which blocks airflow from the victim back towards the rescuer. The breathing tube has a plurality of longitudinally extending strengthening ribs and an integrally molded grid on the bottom thereof to strengthen and rigidize the structure. The plate is a different color than the breathing tube to enhance the perception of safety by a potential rescuer. Alphanumeric information, including precautionary notes and instructions are printed on the transparent shield.

5 Claims, 2 Drawing Sheets

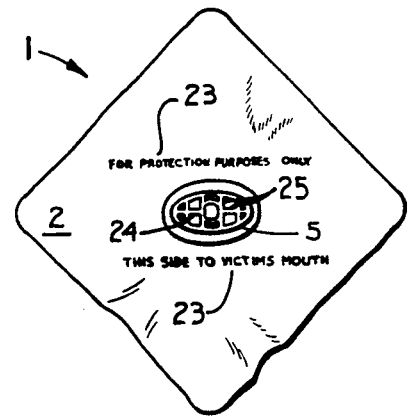
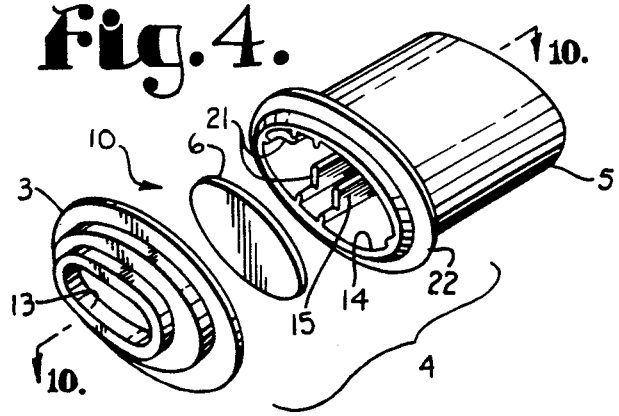
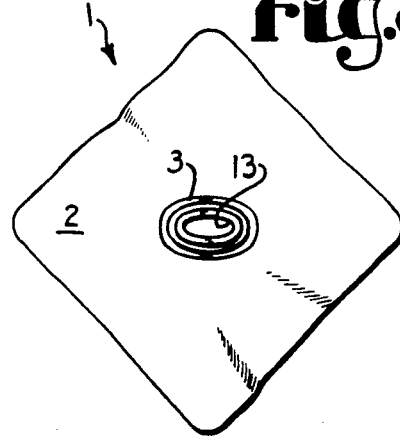

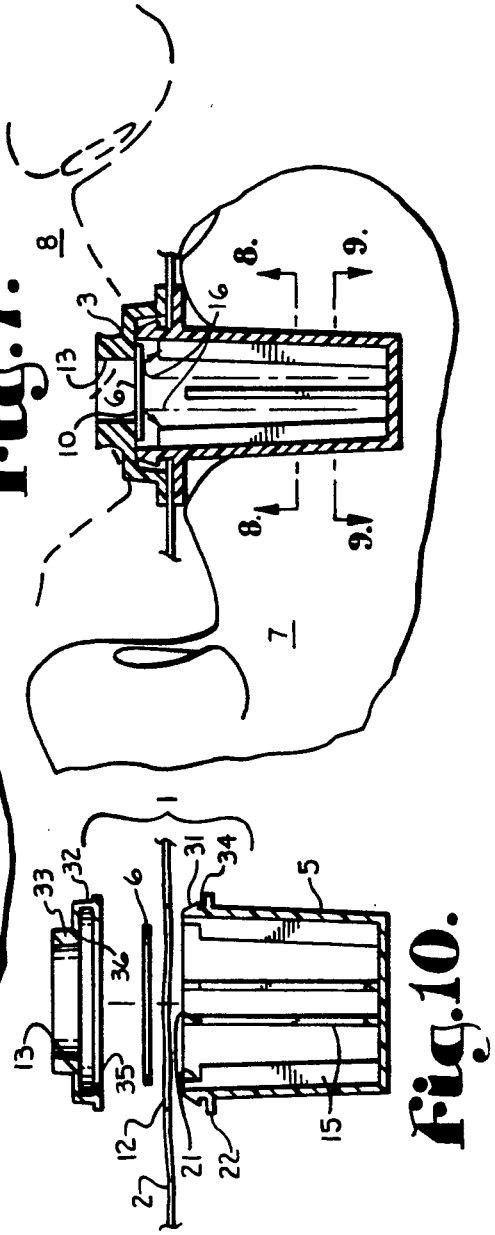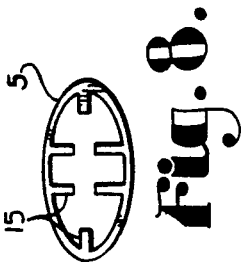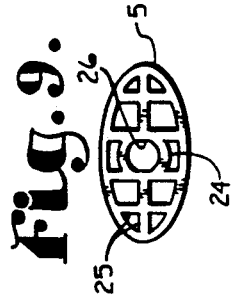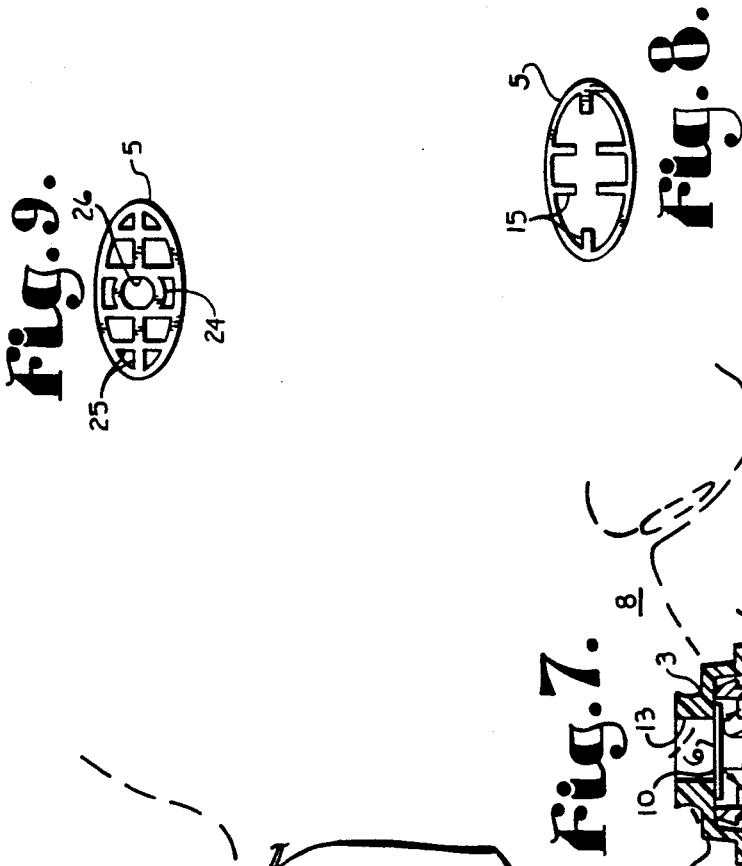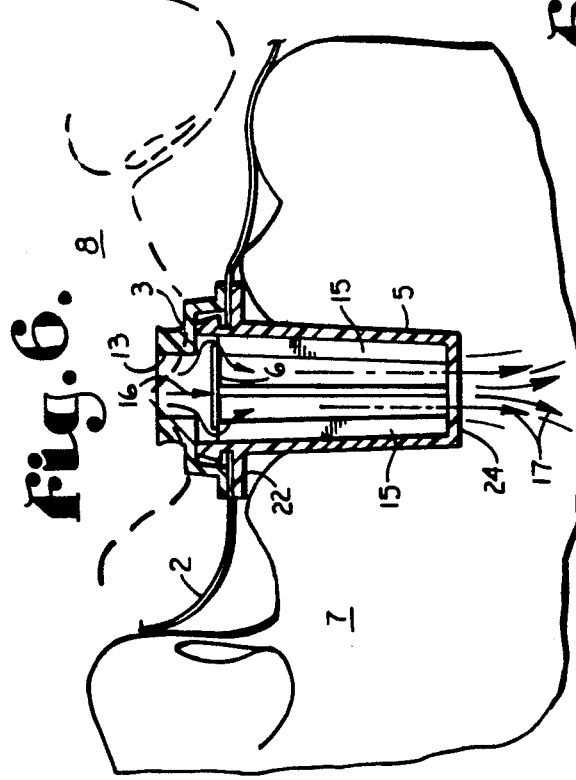

MOUTH-TO-MOUTH WITH VALVE AND BARRIER

BACKGROUND OF THE INVENTION

The present invention relates to a mouth-to-mouth barrier for facilitating mouth-to-mouth resuscitation of a victim who has stopped breathing and for protecting a rescuer engaged in such mouth-to-mouth resuscitation.

Recent widespread dissemination of information and training courses for cardiopulmonary resuscitation (CPR) by the International Red Cross and other organizations has done much to promote the widespread use of this vital life saving technique. CPR, of course, is a technique which combines chest massage with mouth-to-mouth resuscitation in an attempt to revive a victim's interrupted heartbeat and breathing.

Unfortunately, persons conducting CPR are likely to catch communicable diseases from the victim and with the increased number of Acquired Immune Deficiency Syndrome (AIDS) victims which may have blood or other infected body fluids in their mouths, CPR trained individuals and even professional medical practitioners have become reluctant to use mouth-to-mouth resuscitation techniques. This is especially due to the widespread fear, whether justified or not, that the AIDS virus can be transmitted through mouth-to-mouth contact, nevertheless, when blood is present, there is little doubt that contamination can occur. In addition to the fear of contracting AIDS or other communicable diseases, ordinary personal hygiene considerations often delay or prevent timely mouth-to-mouth resuscitation. Numerous devices have been designed in an effort to overcome these problems.

One approach has been to use an air permeable cloth or mesh which is placed over the victim's mouth prior to giving him mouth-to-mouth resuscitation. These devices have tended to impede the flow of air from the rescuer to the victim and limit the effectiveness of resuscitation efforts.

Another approach has been to use an elongated hollow tube which is open at both ends. One end is placed in the victim's mouth while the rescuer places his mouth over the other open end and exhales through the tube to force air into the victim's lungs. While generally an improvement over an air permeable cloth, this approach does not prevent saliva or other liquids or solids from being passed from the victim through the tube to the rescuer.

The effectiveness of these elongated tubes has been enhanced by placing a protective shield around the tubes and by putting one-way check valves inside the tubes. The combination of an extended shield and a one-way valve has greatly reduced the chances of exposure to communicable diseases by a potential rescuer. By making these protective shield and valve equipped tube devices disposable, personal hygiene concerns have also been largely mitigated. Several problems with this basic arrangement remain, however. The hollow tubes have tended to be too flexible, and are thus subject to being closed off if a victim bites down on the tube. The tube's effectiveness can also be compromised if a victim's tongue or any other solid object enters the open end of the tube and blocks the airflow. Furthermore, check valves have generally consisted of flexible flaps which are attached at one end to a portion of the elongate tube, which flaps have tended to be relatively slow in closing. The lack of readily available instructions on the proper use of these devices has also been a drawback.

It is clear then, that a need exists for a reliable, one-way valve and shield equipped mouth-to-mouth resuscitation device which avoids the above cited drawbacks. It is also clear that such a device should be simple and inexpensive to produce by readily available mass production techniques, and that instructions on the proper use of the device should always be immediately accessible.

SUMMARY OF THE INVENTION

The present invention is a mouth-to-mouth barrier for facilitating mouth-to-mouth resuscitation while affording effective protection to a person giving such mouth-to-mouth resuscitation.

The barrier comprises an elongate hollow tube which is elliptical in cross-section. A lip is formed around the circumference near the top of the elongate tube and the top of the tube is placed through an opening near the center of a protective transparent shield which extends for a considerable distance on all sides of the elongate tube. A plurality of strengthening ribs are formed on the inside surface of the tube and extend the length of the tube. The ribs are notched near the top of the tube to accommodate and support a light weight air impermeable disk.

An elliptically-shaped mouthpiece is affixed to the top of the elongate tube, with the light weight disk forming a one-way check valve for an opening in the center of the elliptical mouthpiece. An integrally molded grid is formed across the bottom opening of the elongate tube to provide a barrier to the ingress of solid objects beyond a certain size into the tube. The combined effect of the ribs and the molded grid act to strengthen and rigidize the tube structure, and prevent a victim from inadvertently blocking airflow through the tube by blocking it with his tongue or clamping down on it with his teeth. The light weight disk in combination with the elliptical mouthpiece forms a very fast acting one-way check valve which prevents a victim from exhaling into the rescuer's mouth, while the extended shield directs air and any other matter exhaled or coughed up by the victim away from the face of the rescuer.

OBJECTS AND ADVANTAGES OF THE INVENTION

The principal objects of the present invention are: to provide an improved mouth-to-mouth barrier for facilitating the mouth-to-mouth resuscitation of an accident or heart attack victim; to provide such a barrier which is light weight and inexpensive to produce; to provide such a barrier which is disposable after use; to provide such a barrier which has an effective, fast acting one-way check valve for preventing the victim from exhaling or coughing into the mouth of a rescuer; to provide such a barrier which has an extended transparent shield surrounding an elongate tube incorporating the check valve, which shield prevents the victim from exhaling or otherwise expelling saliva or other material onto the rescuer; to provide such a barrier in which the elongate tube is equipped with longitudinal strengthening ribs; to provide such a barrier in which the elongate tube has a grid integrally formed near an opening which is inserted into the victim's mouth to prevent the victim's tongue from inadvertently blocking the air passage in the tube; to provide such a barrier in which the tube is not subject to being inadvertently crushed by the victim's teeth; and to provide such a barrier which is particularly well adapted for its intended purposes.

Other objects and advantages of this invention will become apparent from the following description taken in conjunction with the accompanying drawings wherein are set forth, by way of illustration and example, certain embodiments of this invention.

The drawings constitute a part of this specification and include exemplary embodiments of the present invention and illustrate various objects and features thereof.

BRIEF DESCRIPTION OF THE DRAWINGS

FIG. 1 is a perspective view of a mouth-to-mouth barrier in accordance with the present invention shown inserted into a victim's mouth.

FIG. 2 is an enlarged bottom plan view of the mouth-to-mouth barrier, illustrating an integrally molded grid.

FIG. 3 is an enlarged top plan view of a mouth-to-mouth barrier, illustrating a rescuer's mouthpiece.

FIG. 4 is an enlarged, exploded perspective view of an elongate breathing tube, including a one-way check valve and a mouthpiece, which tube forms a part of the mouth-to-mouth barrier.

FIG. 5 is an illustration of mouth-to-mouth resuscitation being performed by a rescuer on a victim using a mouth-to-mouth barrier in accordance with the present invention, with that portion of the barrier which is inside the victim's mouth shown in phantom lines.

FIG. 6 is an enlarged, cross-sectional view of the mouth-to-mouth barrier in accordance with the invention, with the one-way check valve shown open and air from the rescuer entering the victim's mouth.

FIG. 7 is another enlarged, cross-sectional view of the mouth-to-mouth barrier, illustrating the check valve closed due to differential pressure produced by air being exhaled by the victim.

FIG. 8 is an enlarged, cross-sectional view of an inside of the elongate tube, illustrating longitudinal ribs, taken along line 8—8 of FIG. 7.

FIG. 9 is an enlarged, cross-sectional view of the inside of the elongate tube, taken along line 9—9 of FIG. 7, and illustrating the integrally molded grid.

FIG. 10 is an enlarged, exploded cross-sectional view of the mouth-to-mouth barrier, taken along line 10—10 of FIG. 4.

DETAILED DESCRIPTION OF THE INVENTION

As required, detailed embodiments of the present invention are disclosed herein; however, it is to be understood that the disclosed embodiments are merely exemplary of the invention, which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure.

Referring to FIG. 1, there is shown a mouth-to-mouth barrier 1 in accordance with the present invention, placed in the mouth of an inert victim 7 and ready for use in mouth-to-mouth resuscitation of the victim 7. The barrier consists of a transparent shield 2 which covers a substantial portion of the victim's face and an elongate breathing tube 4 (FIG. 4), of which an oval mouthpiece 3 is clearly visible in FIG. 1. The transparent shield 2 is sandwiched between the mouthpiece 3 and an insert portion 5 of the breathing tube 4 with a top flange 11 of the insert portion 5 extending through a mating aperture 12 (FIG. 10) in the shield 2. The shield 2 and the insert portion 5 are securely attached to one another, as will be later described with reference to FIG. 10.

Referring to FIG. 4, a one-way valve 10, comprises a light weight air impermeable plate 6 and a restricted opening 13 in the mouthpiece 3 and permits air to flow from the mouth of a rescuer 8 into the mouth of the victim 7 but does not permit airflow in reverse, i.e. from the victim 7 back toward the rescuer 8. This one-way valve action is accomplished by allowing the flexible plate 6 to freely travel between two valve support positions. When the rescuer 8 breathes into the breathing tube 4, the differential force of his breath pushes the plate 6 downward (as is seen in FIG. 6) until it rests on a plurality of ledges 21 formed in a series of axially extending and longitudinal ribs 15 in the insert portion 5. The plate 6 is smaller in area than an upper opening 14 in the top of the insert portion 5, thus allowing air to flow around the plate 6 and through the insert portion 5. When air pressure is exerted on the bottom of the insert portion 5, as by the victim 7 coughing or exhaling, the plate 6 is urged upward into contact with the inside of the mouthpiece 3, blocking off the opening 13 and preventing air from flowing back towards the rescuer 8 (as is seen in FIG. 7). A molded flange 22 surrounds the insert portion 5 to prevent the shield 2 (FIG. 10) from sliding downward over the insert portion 5.

FIG. 2 is a bottom view of the mouth-to-mouth barrier 1, illustrating the bottom of the transparent shield 2 and the bottom of the insert portion 5 of the breathing tube 4. As shown, the transparent shield 2 can be printed with vital information indicia 23 of interest to the rescuer 8, including cautionary safety messages and/or instructions. The bottom of the insert 5 includes an integrally molded grid 24 which comprises a plurality of transversely extending cross-members 25. The grid 24 acts to prevent the victim's tongue from entering the breathing tube 4 and inadvertently blocking airflow from the rescuer. In addition, the grid 24, along with the longitudinal ribs 15 (FIG. 4) in the insert portion 5, act to give strength and rigidity to the breathing tube 4, making the barrier extremely durable and also resistant to collapse, should the victim 7 bite down on the breathing tube 4. The transparent shield 2, as illustrated in FIG. 1, acts to prevent saliva or other exhaled or coughed material that originates from the victim 7 from being expelled onto the face of the rescuer 8.

FIG. 3 is a top view of the mouth-to-mouth barrier 1, illustrating the placement of the breathing tube 4 including the mouthpiece 3 in the protective shield 2. As can be seen in FIG. 3, the restricted opening 13 is considerably smaller than the outside circumference of the breathing tube 4, which enables the plate 6 to block the mouthpiece 3, but not the insert portion 5 of the breathing tube 4.

FIG. 5 illustrates a recommended position for the rescuer 8 to assume in giving mouth-to-mouth resuscitation using the barrier 1. The insert portion 5 of the breathing tube 4 is shown partially in phantom lines to indicate the distance that it extends into the mouth of the victim 7.

FIG. 6 illustrates the flow of air from the rescuer's mouth into the mouth of the victim 7 through the breathing tube 4. The solid arrow 16 near the top of the breathing tube 4 indicates the force being exerted against the plate 6 by air being exhaled by the rescuer. The hollow arrows 17 indicate the flow of air around the plate 6 and through the breathing tube 4 and into the mouth of the victim 7.

FIG. 7 illustrates pressure being exerted against the plate 6 (again note the solid arrows 16) should the victim 7 attempt to exhale through the breathing tube 4. The upward pressure of air from the victim's breath urges the plate 6 into contact with a ledge 36 inside the mouthpiece 3, blocking off airflow through the restricted opening 13. This prohibits exhaled or coughed material from reaching the mouth of the rescuer 8 from the victim 7.

FIG. 8 is a cross-sectional view of the insert portion 5 of the breathing tube 4, taken along line 8—8 of FIG. 7. FIG. 8 clearly illustrates the strengthening ribs 15 which are integrally molded into the insert portion 5. FIG. 9 is another cross-sectional view of the insert portion 5 of the breathing tube 4, taken along 9—9 of FIG. 7. FIG. 9 illustrates the integrally molded grid 24 which comprises a plurality of transversely extending cross-members 25, preferably with a centralized opening 26 formed therein to promote efficient airflow.

FIG. 10 is an exploded cross-sectional view of the barrier 1, taken along line 10—10 of FIG. 4, with a portion of the transparent shield 2 illustrated as well. During assembly, the oval opening 12 in the transparent shield 2 is forced over a small angled lip 31 which extends around the top of the insert portion 5, where it engages a recess 34 formed in the insert portion 5 between the small angled lip 31 and the flange 22. The plate 6 is then placed through the opening 12 in the transparent shield 2 and rests on the ledges 21 formed in the ribs 15 in the insert portion 5. The mouthpiece 3 is then adhesively secured to the top of the insert portion 5 and the top of the transparent shield 2, resulting in a secure, air-tight structure. The mouthpiece 3 comprises a smaller diameter upper portion 33 and a larger diameter lower portion 32 which form the internal ledge 36 where they are joined. The ledge 36 acts as a stop for the plate 6 when it is forced upward by air pressure from a victim's breath.

The transparent shield 2 is made of a flexible plastic material such as a film-forming thermoplastic which is generally impermeable to ordinary bodily fluids. Examples of such material include polyvinyl chlorides, polyethylene, polypropylene, etc. The remainder of the barrier 1, including the mouthpiece 3 and the insert portion 5 are formed of a rigid molded plastic. The plate 6 is formed of rigid plastic, but is much thinner and of lighter weight than either the mouthpiece 3 or the insert portion 5. The flexible plate 6 can also be a different color than either the mouthpiece 3 or the insert portion 5. For example, if the mouthpiece 3 and the insert portion 5 are formed of ordinary semi-transparent white plastic, the flexible plate 6 can be green in color and opaque, which acts to enhance the perceived effectiveness of the mouth-to-mouth barrier 1. This is due to the fact that the potential rescuer, when viewing the barrier from the mouthpiece end, sees only the green plate 6, giving him or her an enhanced perception of the blocking effectiveness of the barrier 1.

While the transparent shield 2 has been illustrated as generally square, it should be apparent that other shapes such as a circle or an ellipse could be equally effective. Furthermore, the cross-sectional shape of the molded grid 24 and the number and placement of the strengthening ribs 15 are merely illustrative and other arrangements can be effectively used.

It is to be understood that while certain forms of the present invention have been illustrated and described herein, it is not to be limited to the specific forms or arrangement of parts described and shown.

What is claimed and desired to be secured by Letters Patent is as follows:

1. A mouth-to-mouth barrier for facilitating mouth-to-mouth resuscitation of a victim while providing protection for a rescuer, comprising a transparent protective shield and an elongate breathing tube extending through an opening in said shield, wherein:
    (a) the breathing tube comprises an insert portion adapted for insertion in the victim's mouth and a mouthpiece portion adapted for placement in the rescuer's mouth; the mouthpiece portion has a smaller diameter upper portion that is open at the top and a larger diameter lower portion is open at the bottom; said upper and lower portions being connected together to form a first internal ledge therebetween;
    (b) an air impermeable plate is positioned within said insert portion;
    (c) said insert portion includes a second internal ledge sized and positioned to support said plate near the top of said insert portion; said plate is sized to permit airflow around said plate when said plate is supported by said second ledge, but blocks airflow through said top opening in said smaller diameter upper portion of said mouthpiece when said plate is positioned against said first ledge;
    (d) said plate acts as a one-way valve to permit airflow from said rescuer to said victim but blocks airflow from said victim to said rescuer;
    (e) said insert portion further includes a plurality of axially extending strengthening ribs formed on the interior surface thereof and extending along the length thereof; and
    (f) said second internal ledge in said insert portion is formed by notches in said ribs near the top of said insert portion.

2. A mouth-to-mouth barrier as claimed in claim 1, wherein:
    (a) said insert portion has an integrally molded grid partially covering an opening at the bottom thereof, said grid comprising a plurality of transversely extending cross-members; whereby
    (b) said grid is adapted to prevent solids of a certain size, including the victim's tongue, from entering said insert portion and blocking said tube or said valve, and the combination of said ribs and said grid operably function to strengthen and rigidize said breathing tube to prevent collapse of said tube, should the victim bite down on said tube.

3. A mouth-to-mouth barrier as claimed in claim 1, wherein:
    (a) said plate is of a different color than said breathing tube to enhance a rescuer's perception of safety.

4. A mouth-to-mouth barrier as claimed in claim 1, wherein:
    (a) said transparent shield has alphanumeric information printed thereon which information includes precautionary notes and/or instructions on the use of said barrier.

5. A mouth-to-mouth barrier for facilitating mouth-to-mouth resuscitation of a victim while providing protection for a rescuer, comprising a transparent protective shield and an elongate breathing tube extending through an opening in said shield, wherein:

(a) the breathing tube comprises an inert portion adapted for insertion in the victim's mouth and a mouthpiece portion adapted for placement in the rescuer's mouth; the mouthpiece potion having a smaller diameter upper portion which is open at the top and a larger diameter lower portion which is open at the bottom; said upper and lower portions being connected together to form a first internal ledge therebetween;

(b) an air impermeable plate positioned within said insert portion;

(c) said insert portion including a second internal ledge sized and positioned to support said plate near the top of said insert portion, said plate being sized to permit airflow around said plate when said plate is supported by said second ledge, but to block airflow through said opening in said smaller diameter upper portion of said mouthpiece, when said plate is positioned against said first ledge; said plate acting as a one-way valve to permit airflow from said rescuer to said victim but to block airflow from said victim to said rescuer;

(d) said insert portion including a plurality of strengthening ribs formed on the interior surface thereof, said strengthening ribs extending along the length thereof;

(e) said second internal ledge in said insert portion being formed by notching said ribs near the top of said insert portion;

(f) said insert portion having an integrally molded grid partially covering an opening at the bottom thereof, said grid comprising a plurality of transversely extending cross-members, said grid adapted to prevent solids of a certain size, including the victim's tongue, from entering said insert portion and blocking said tube or said valve, and the combination of said ribs and said grid act to strengthen and rigidize said breathing tube to prevent collapse of said tube, should the victim bite down on said tube;

(g) said plate being a different color than said breathing tube to enhance a rescuer's perception of safety; and (h) said transparent shield having alphanumeric use information printed thereon.

* * * * *